United States Patent [19]

Oshima et al.

[11] Patent Number: 5,112,202

[45] Date of Patent: May 12, 1992

[54] TURBO PUMP WITH MAGNETICALLY SUPPORTED IMPELLER

[75] Inventors: Saburo Oshima; Tsugito Nakazeki, both of Shizuoka; Teruaki Akamatsu, Kyoto; Motoharu Niki, Nara, all of Japan

[73] Assignee: NTN Corporation, Osaka, Japan

[21] Appl. No.: 644,777

[22] Filed: Jan. 23, 1991

[30] Foreign Application Priority Data

| Jan. 31, 1990 | [JP] | Japan | 2-22849 |
| Oct. 11, 1990 | [JP] | Japan | 2-274656 |
| Oct. 11, 1990 | [JP] | Japan | 2-274657 |

[51] Int. Cl.[5] .................... F04B 17/00; F04B 35/04; F03B 13/00
[52] U.S. Cl. ............... 417/423.7; 417/423.1; 417/356; 415/900
[58] Field of Search .......... 417/423.1, 423.7, 420, 417/355, 356; 415/900

[56] References Cited

U.S. PATENT DOCUMENTS

| 3,107,310 | 10/1963 | Carriere et al. |   |
| 3,575,536 | 4/1971 | Jacobs et al. |   |
| 4,642,036 | 2/1987 | Young. |   |
| 4,643,641 | 2/1987 | Clausen et al. | 415/900 |
| 4,688,998 | 8/1987 | Olsen et al. | 415/900 |
| 4,806,080 | 2/1989 | Mizobuchi et al. |   |
| 4,850,821 | 7/1989 | Sakai | 417/420 |
| 4,944,748 | 7/1990 | Bramm et al. | 417/356 |
| 4,948,348 | 8/1990 | Doll et al. |   |
| 4,984,972 | 1/1991 | Clausen et al. | 417/420 |

FOREIGN PATENT DOCUMENTS

| 1063035 | 8/1955 | Fed. Rep. of Germany. |
| 1165144 | 1/1964 | Fed. Rep. of Germany. |
| 3523343 | 6/1985 | Fed. Rep. of Germany. |
| 2138832 | 8/1971 | Fed. Rep. of Germany. |

OTHER PUBLICATIONS

Kreisel-pumpen, Lexikon, p. 313.
Kreiselpumpen, by Troskolanski et al., pp. 301-302.

*Primary Examiner*—Richard A. Bertsch
*Assistant Examiner*—Alfred Basichas
*Attorney, Agent, or Firm*—Lowe, Price, LeBlanc & Becker

[57] ABSTRACT

A turbo pump is disclosed, having a magnetically supported impeller. The turbo pump includes a casing (31) made of a non-magnetic material, an impeller (32) provided in the casing (31), a triaxial controlled magnetic bearing provided outside of the casing (31) for magnetically supporting the impeller (32), and a rotor (37) magnetically coupled to the impeller (32) for rotating the impeller. The triaxial controlled magnetic bearing includes a magnetic member (35) provided on one plane of the impeller and a plurality of electromagnets (39) provided in the casing in such a way as to be opposed to the magnetic member. Coupling between the impeller (32) and the rotor (37) is effected by a plurality of permanent magnets (33, 38) respectively provided thereon. In another aspect of the invention, a plurality of stator windings for generating the rotating magnetic field may be provided on the side of the stator in place of rotating means utilizing a magnetic coupling.

15 Claims, 7 Drawing Sheets

TURBO PUMP WITH MAGNETICALLY SUPPORTED IMPELLER

BACKGROUND OF THE INVENTION

1. Field of the Invention

The invention relates generally to turbo pumps, and, more particularly, turbo pumps having an impeller magnetically supported in a casing from outside of the casing without being mechanically supported.

2. Description of the Background Art

A turbo pump is a pump for providing energy to fluid by way of the rotation of the impeller, and widely known in the industrial world.

FIGS. 1 and 2 are sectional views showing a conventional turbo pump used in biotechnology, semiconductor manufacturing technologies, and medical instruments, etc. Referring to FIG. 1, a pump 10 includes an impeller 11 for providing a rotary motion to the fluid. The impeller 11 is mechanically supported by a rotating shaft 12, with the rotating shaft 12 being supported by a rolling bearing 13 and driven by a motor 14. When the rotating shaft 12 is rotated by the motor 14, the impeller 11 mechanically supported at the rotating shaft 12 rotates. By the rotation of the impeller 11, the fluid is sucked from a suction tube 16, and then discharged through a scroll chamber 17.

A pump used in biotechnology, semiconductor manufacturing technologies, and medical instruments is required to be extremely clean. Accordingly, in the pump 10 shown in FIG. 1, in order to isolate the fluid from the rolling bearing 13 and the motor 14 generating contaminants which contaminate the fluid, a seal 15 is provided between the impeller 11 and the bearing 13. The seal 15 is, however, in contact with the rotating shaft 12, so that there are disadvantages that the fluid may be contaminated by the contaminants generated in this contacting portion, and that the fluid may change in quality by the frictional heat. In addition, it is impossible for the seal 15 to completely prevent the contaminants produced from the bearing 13 and the motor 14 from entering the fluid.

In order to eliminate these disadvantages, there is shown a pump 20 in FIG. 2, having a magnetic bearing instead of a rolling bearing, an electromagnet of a motor, etc. being sealed, and a portion made of iron or iron member being plated, so that no seal is required.

Referring to FIG. 2, a rotating shaft 22 for an impeller 21 is supported by a radial magnetic bearing 23 and an axial magnetic bearing 24, and rotated by a motor 25. While the fluid enters the spindle 26, it is not contaminated as the iron member or the coil of the motor 25 and the magnetic bearings 23, 24 is sealed or plated.

In the pump shown in FIG. 2, however, there is a place where the fluid stagnates in the spindle 26, so that it is not preferable to apply such a pump to biotechnology and medical instruments. For example, if it is applied to an artificial heart, there occur thrombi due to the stagnation of the blood, so that the life is endangered.

SUMMARY OF THE INVENTION

One object of the invention is to provide a turbo pump capable of feeding a fluid without stagnation, and keeping it clean at the same time.

In short, the present invention provides a pump including a rotating member having blades providing energy to a fluid, and adapted to be capable of receiving magnetic action from the outside, a casing for housing the rotating member, means for supporting the rotating member from outside of the casing in a manner non-contacting to the casing, and means for rotating the rotating member by the magnetic action from outside of the casing.

The means for supporting the above-mentioned rotating member in a non-contacting way may be preferably a 3-axis controlled magnetic bearing. The 3-axis controlled magnetic bearing includes a plurality of permanent magnets or electromagnets provided on a rotation driving member, a plurality of permanent magnets provided on one plane of the rotating member to be in an attracting relationship with the permanent magnets or electromagnets of the rotation driving member over the casing, a magnetic member provided on the other plane of the rotating member, and a plurality of controlled electromagnets for generating a force attracting the magnetic member, so that balancing with the attracting force is provided between the above-mentioned magnets.

The means for rotating the above-mentioned rotating member by the magnetic action may be rotatable rotation driving means magnetically coupled to the rotating member, or may be a plurality of stator windings provided on a stator for generating a rotating magnet field. In the case in which a plurality of stator windings are employed, the 3-axis controlled magnetic bearing includes the stator having the stator windings, a plurality of permanent magnets provided on one plane of the rotating member to be in an attracting relationship with the stator, a magnetic member provided on the other plane of the rotating member, and a plurality of controlled electromagnets for generating a force attracting the magnetic member, so that balancing with the attracting force is provided between the stator and the magnets of the rotating member.

In accordance with the invention, the rotating member having blades providing energy to a fluid is supported in a non-contacting manner without being mechanically supported in a casing, so that the contamination of the fluid is prevented.

The rotating member does not have a shaft for being mechanically supported on, making the configuration of the casing smaller, so that the configuration of the pump may be made compact.

In addition, there occur no solidification of fluid and deposition of impurities as there is no place where the fluid stagnates in the pump in accordance with the present invention.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

A First Embodiment

In accordance with a first embodiment, as will be described in the following, an impeller is supported by a 3-axis controlled magnetic bearing, and rotated by the rotation of a magnetically coupled rotor.

Figure 1:
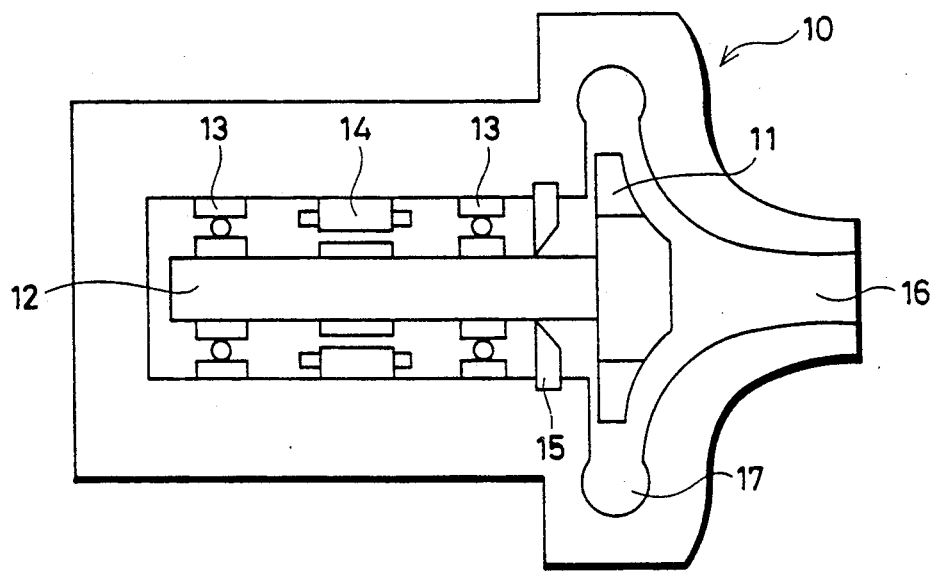
FIG. 1 is a sectional view showing a conventional turbo pump.
Figure 2:
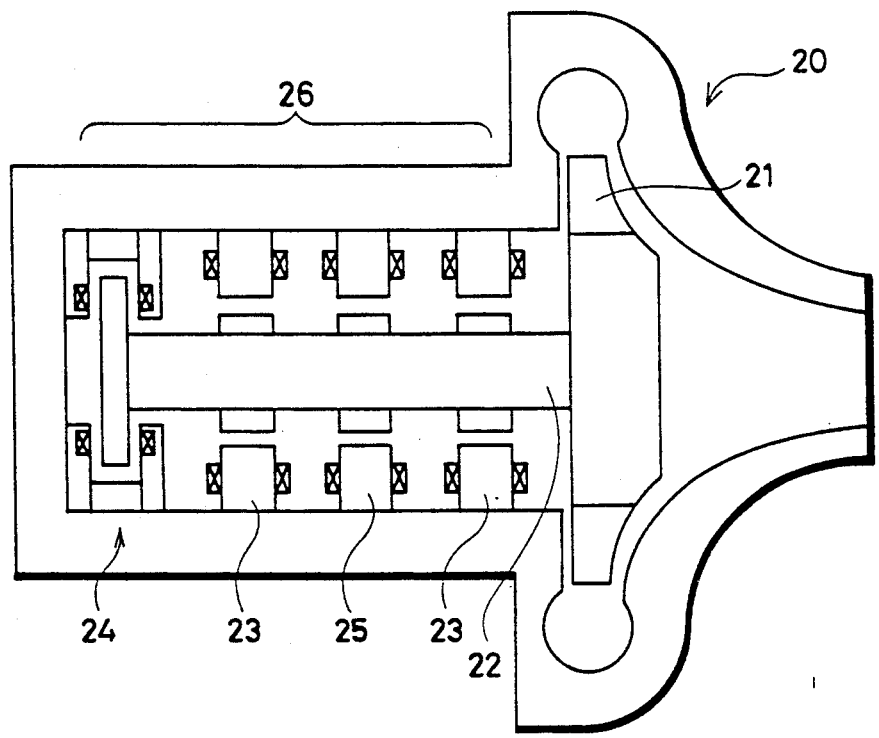
FIG. 2 is a sectional view showing another conventional turbo pump.
Figure 3:
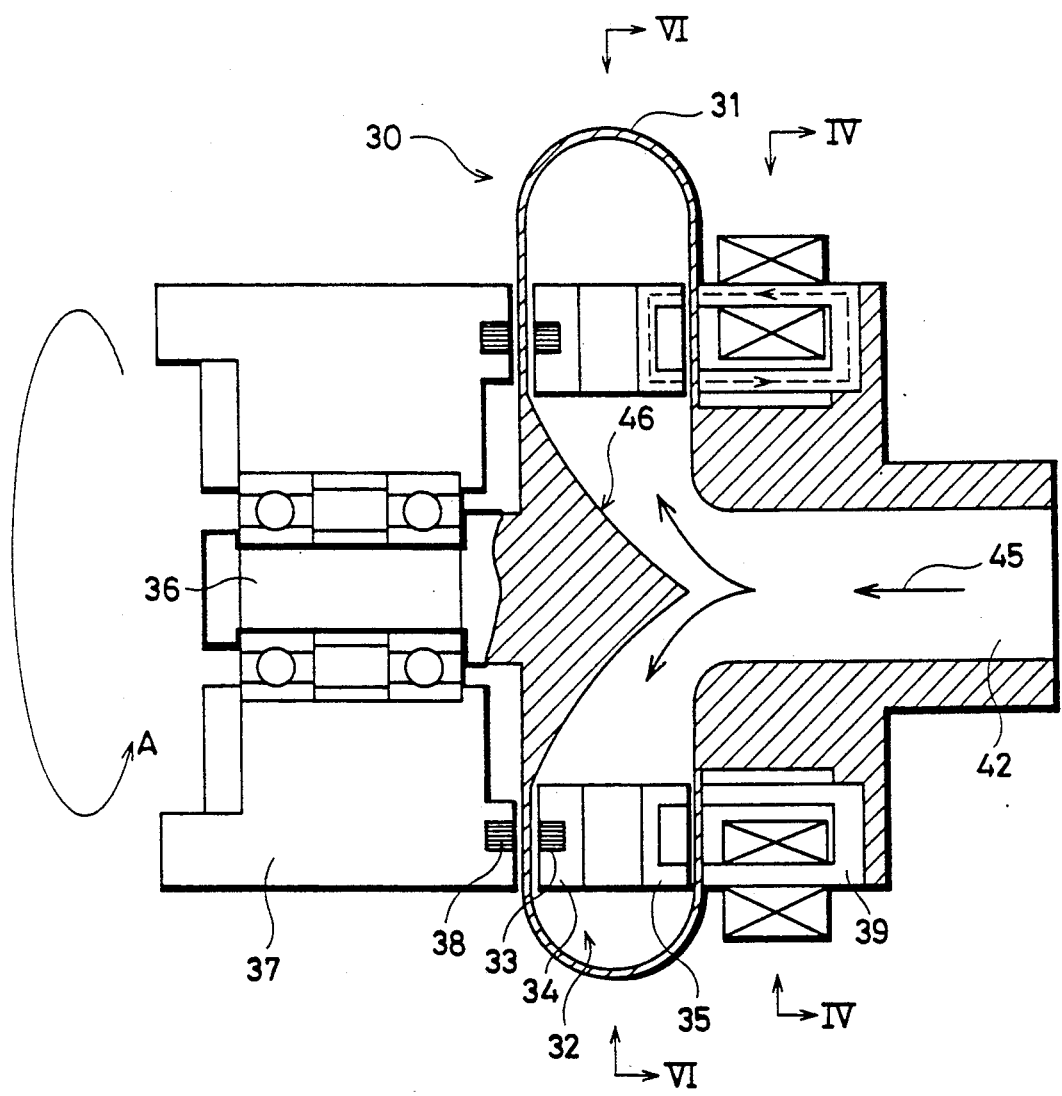
FIG. 3 is a sectional view showing a turbo pump in accordance with a first embodiment of the present invention.

Referring to FIG. 3, an impeller 32 is provided in a casing 31 of a pump 30. The casing 31 is made of a non-magnetic material. The impeller 32 includes a non-magnetic member 34 having blades providing energy to a fluid and a plurality of permanent magnets 33, and a soft iron member 35 corresponding to a rotor of a controlled magnetic bearing, which are coupled together by a rivet and so on. The impeller 32 has no shaft for pivoting itself. The soft iron member 35 has its surface treated so as not to produce rust and so on. The permanent magnets 33 are arranged on a circumference surrounding the center point of the impeller 32, at predetermined intervals. The magnets adjacent to each other are magnetized such that the directions of the magnetic fields are opposite to each other. A rotor 37 mechanically supported on a shaft 36 is provided outside of the casing 31, opposed to the side having the permanent magnet 33 of the impeller 32. The rotor 37 is driven by a motor (not shown), and rotates itself in the direction shown by an arrow A in FIG. 3. The same number of permanent magnets 38 as the permanent magnets of the impeller are attached to the rotor 37 such that they are opposed to the permanent magnets 33 of the impeller 32, and an attracting force may act on them. The permanent magnets 38 are magnetically coupled to the permanent magnets 33. Instead of the permanent magnets 38, electromagnets may be used.

Figure 4:
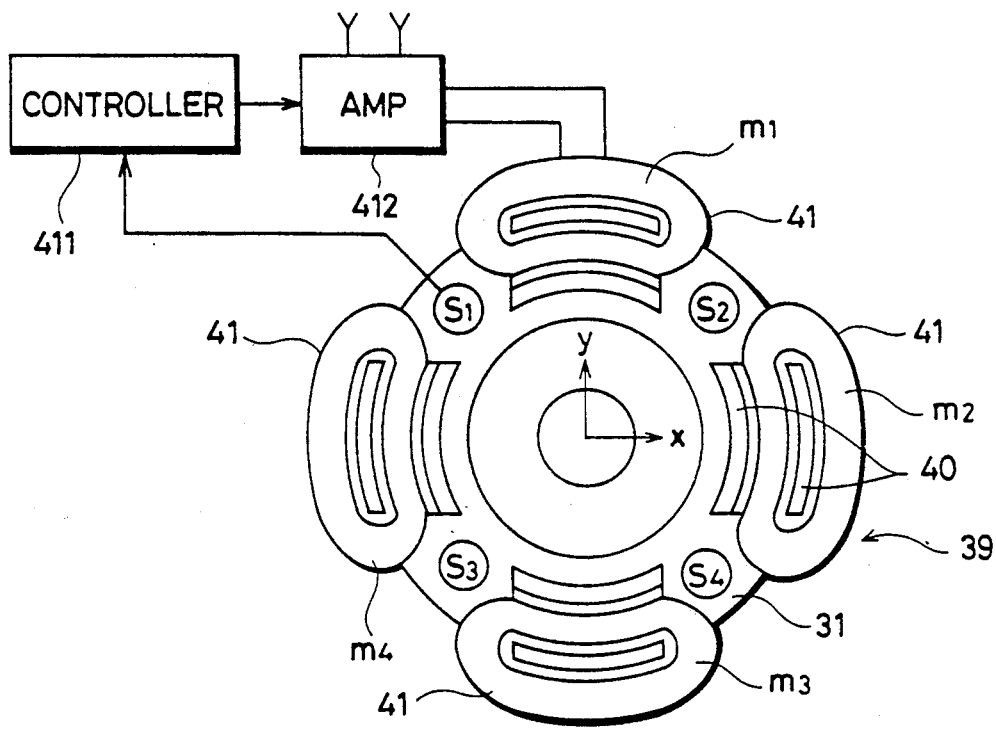
FIG. 4 is a sectional view along the line IV—IV shown in FIG. 3.
Figure 5:
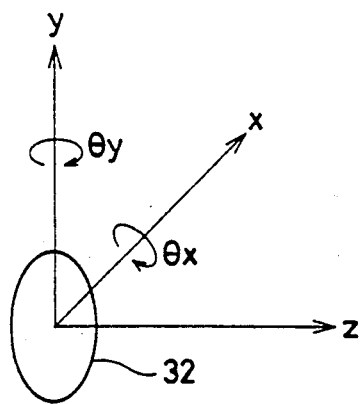
FIG. 5 is a view for describing the control of the position of the impeller shown in FIG. 3.

Opposing to the side having the soft iron member 35 of the impeller 32, an electromagnet 39 is attached to the casing 31, which acts to balance with the attracting force of the permanent magnets 33, 38 so as to hold the impeller 32 in the center of the casing 31. In accordance with the embodiment, 4 electromagnets 39 are provided as represented by the reference designations m1 to m4 in FIG. 4. It is necessary to provide at least 3 electromagnets in order to balance the force in the direction of the coordinate axis z (axial direction), and make 0 the moment around the x axis and the y axis orthogonal to the z axis as shown in FIG. 5. Preferably, as shown in FIG. 4, each of the electromagnets 39 includes a pair of 2 yokes 40, and a coil 41 coiled around the yokes. The electromagnet 39 is preferably sealed, thereby reducing the increase in the temperature due to the heat of generated by electromagnet 39.

Position sensors s1 to s4 each are provided between two adjoining electromagnets. The position sensors s1 to s4 detect the clearance between the electromagnet 39 and the soft iron member 35. The detection output is fed back to a controller 411 controlling an amplifier 412 for supplying a current to the coil 41. More specifically, the control of the position in the z axis direction may be conducted, for example, by adjusting the magnitude of the current supplied to the electromagnets m1, m2, m3 and m4. The control of the moment around the x axis may be conducted, for example, by adjusting the current supplied to the electromagnet m1 and the current supplied to the electromagnet m3. The control of the moment around the y axis may be conducted, for example, by adjusting the current supplied to the electromagnet m2 and the current supplied to the electromagnet m4. As a result, z, $\theta_x$, $\theta_y$, shown in FIG. 5 are controlled, holding the impeller 32 in the center of the casing 31 in such a floating manner as it is spaced from the casing 31 with a predetermined space between them.

Even if a stress in a radial direction is imposed on the impeller 32 by some action, the impeller 32 is held in the center of the casing 31 as the force in the radial direction is moderated by a shearing force of the magnetic flux between the permanent magnet 33 and the permanent magnet 38 and a shearing force of the magnetic flux between the electromagnet 39 and the soft iron member 35 (shown in a broken line in FIG. 3).

Figure 6:
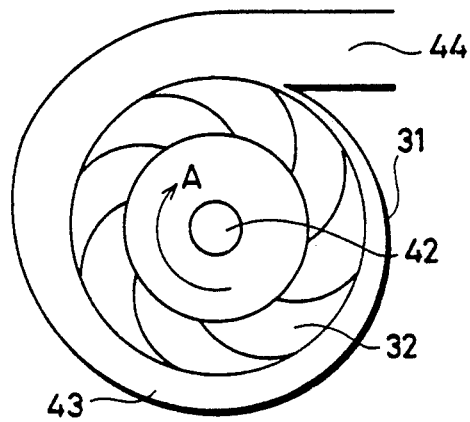
FIG. 6 is a sectional view along the line VI—VI shown in FIG. 3.

When the rotor 37 rotates with the impeller 32 being magnetically supported, i.e., floating in the casing 31, the permanent magnet 33 and the permanent magnet 38 are magnetically coupled together, so that the impeller 32 rotates in the direction of the arrow A as shown in FIGS. 3 and 6. Referring to FIG. 6, one scroll chamber 43 is provided in the casing 31, surrounding the impeller 32. The scroll chamber 43 has such a configuration that the cross-sectional area of the fluid passage is gradually increased from the upstream side to the downstream side of the fluid, so that the fluid flows smooth. The fluid is sucked from a suction port 42, and then fed through a scroll chamber 43 into a discharge port 44.

As shown in FIG. 3, while the flow 45 in the central portion of the suction port has a force in the direction of the center axis, the impeller 32 is not acted on by the force in the axial direction by the flow because a flow uniforming guide 46 is provided such that the flow may be only in the radial direction.

The impeller 32 is isolated from the rotor 37 and the electromagnet 39 by the casing 31, so that the fluid is not contaminated by them, thereby keeping clean the fluid ejected from the pump 30.

It is possible to reduce the volume of the casing as only the impeller that is not mechanically supported is provided in the casing 31. The pump therefore may be made smaller.

In addition, the fluid does not stagnate in the pump 30, producing no solidification of the fluid nor the deposition of impurities. Even if the pump is applied in an artificial heart and so on, it produces no thrombus.

Figure 7:
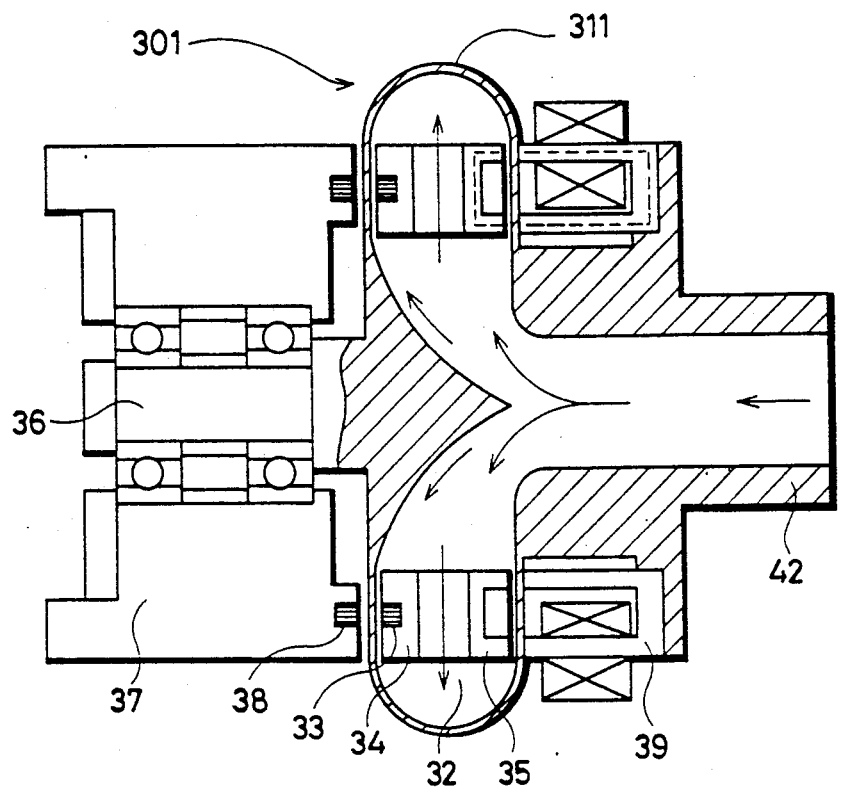
FIG. 7 is a sectional view showing a modified example of the first embodiment of the present invention.
Figure 8:
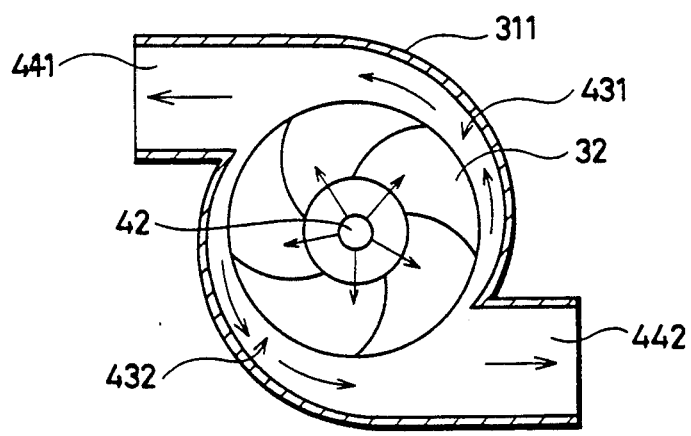
FIG. 8 is a sectional view showing the structure of a scroll chamber of the turbo pump shown in FIG. 7.

FIG. 7 shows a turbo pump representative of a modified example of the first embodiment. FIG. 8 shows the structure of the scroll chamber of the turbo pump shown in FIG. 7.

Referring to FIGS. 7 and 8, in the casing 311, there are provided 2 scroll chambers 431, 432 symmetrically on the periphery of the impeller 32. Each of the 2 scroll chambers has such a configuration that the cross-sectional area of the fluid passage is gradually increased from the upstream side to the downstream side of the fluid. An outlet port 441 connecting to the scroll chamber 431 and an outlet port 442 connecting to the scroll chamber 432 are arranged symmetrically with respect to the center axis of the impeller 32. When the impeller 32 rotates, the fluid is sucked from the suction port 42, and then sent past the scroll chambers 431, 432 into the outlet ports 441, 442. There may be 3 or more scroll chambers provided. In that case, each scroll chamber is provided to have an angle of "360° the number of scroll chambers" with respect to each other.

When a plurality of scroll chambers are arranged symmetrically with respect to the center of the impeller as described above, the forces in the radial direction which act on the impeller balance, so that the position of the axis of rotation of the impeller does not shift. The impeller therefore may rotate in an extremely stable manner.

Figure 9:
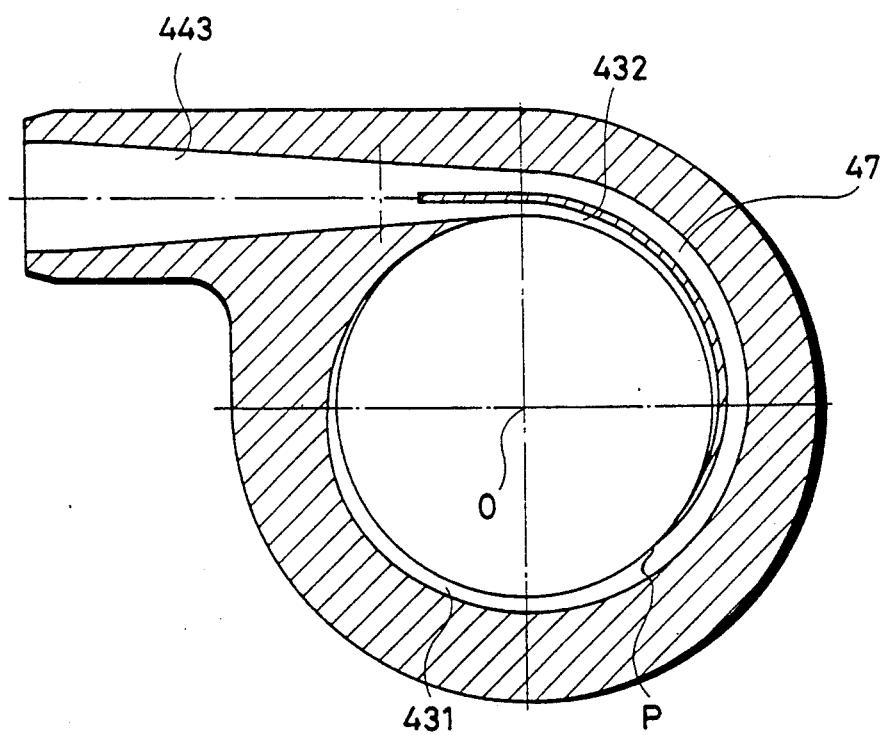
FIG. 9 is a sectional view showing the structure of another scroll chamber applied in a turbo pump in accordance with the present invention.

FIG. 9 shows another modified example of a scroll chamber.

Referring to FIG. 9, a scroll chamber 431 and a scroll chamber 432 having the same configuration as that of the scroll chamber 431 are provided symmetrically with respect to the center O. The scroll chamber 431 is connected, at a point P, to a fluid passage 47 extending to an outlet port 443. The scroll chamber 432 is extending to the outlet port 443. The fluid via the scroll chamber 431 and the fluid passage 47 merges with the fluid via the scroll chamber 432 in the outlet port 443. The fluid passage 47 has a cross-sectional area larger than the maximum fluid passage cross-sectional area of the scroll chamber, thereby reducing the resistance in the fluid passage 47. When the configuration as shown in FIG. 9 is adopted, the appearance of the pump is made simplified.

A Second Embodiment

In a second embodiment, as well as the first embodiment, the impeller is supported by a 3-axis controlled magnetic bearing. Means for rotating the impeller is different from that in the first embodiment, and includes a plurality of stator windings for generating rotating magnetic field on the side of a stator.

Figure 10:
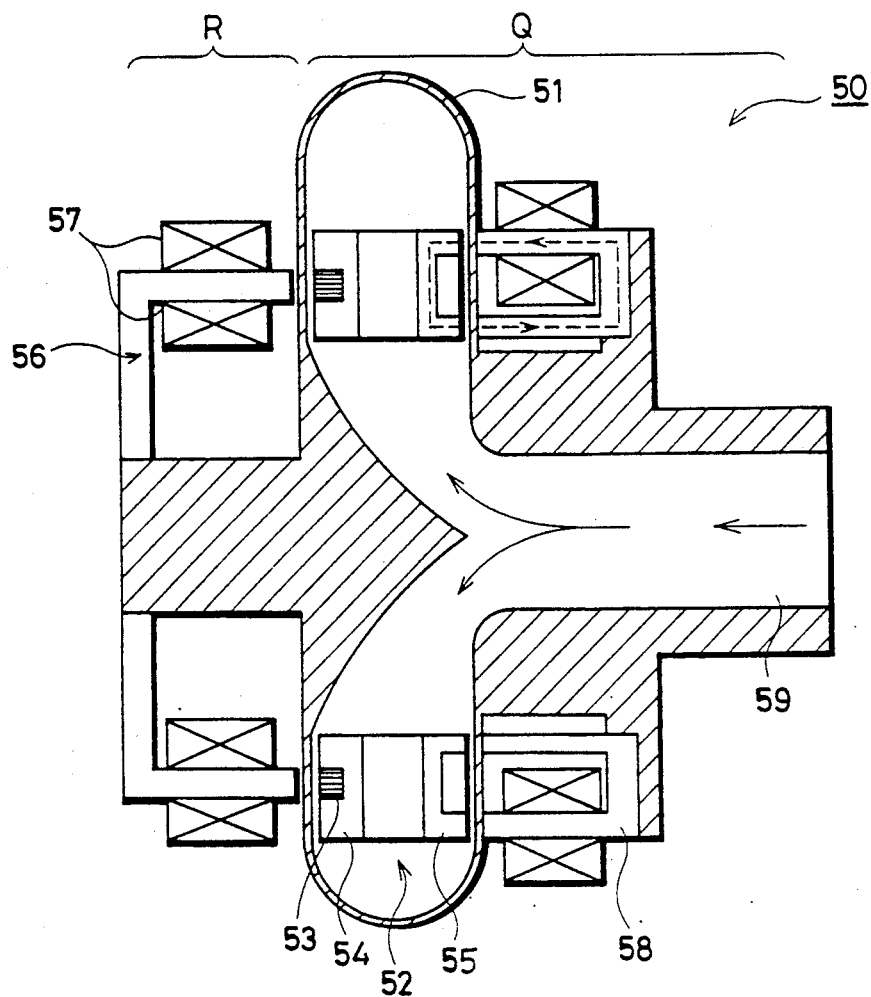
FIG. 10 is a sectional view showing a turbo pump in accordance with a second embodiment of the present invention.
Figure 11:
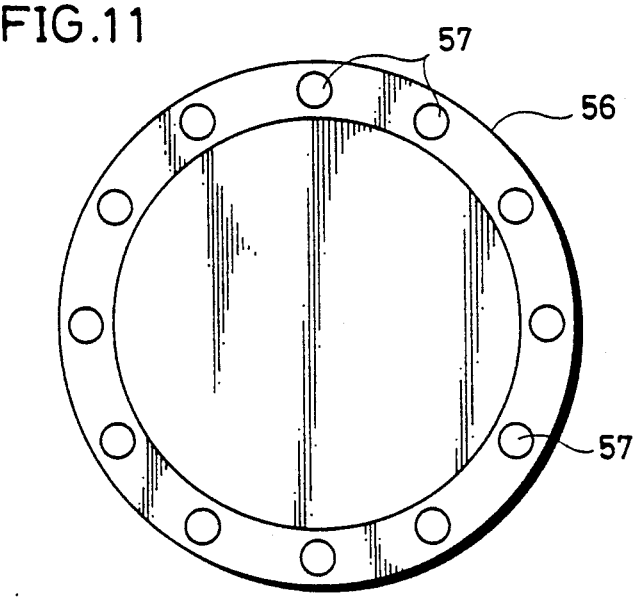
FIG. 11 is a plan view showing the structure of the stator shown in FIG. 10.

Referring to FIG. 10, a casing 51, an impeller 52, permanent magnets 53, a non-magnetic member 54, a soft iron member 55 and electromagnets 58 in the Q portion are respectively the same as corresponding sections shown in FIG. 3, so that the description thereof is not repeated. A plurality of stator windings 57 are arranged on a predetermined circumference of a stator 56 in the R portion as shown in FIG. 11. The number of permanent magnets 53 on the side of the impeller 52 is 1.5 times of the number of stator windings 57. On the side of the stator 56, a sensor (not shown) for detecting the position of the rotating impeller 52 is provided. The magnetic field rotates in response to a non-contact type control commutator, for example, a thyristor (not shown) connected to each stator winding 57 being turned on/off according to the detected position, thereby causing the impeller 52 provided with the permanent magnet 53 to rotate.

The impeller 52, as in the first embodiment, is supported in the casing 51, being spaced from the casing 51 with a predetermined space between them by the action of the electromagnet 58.

In a magnetically supported manner, the impeller 52 rotates when the magnetic field on the side of the stator 6 is rotated, thereby causing the fluid to be sucked from the suction port 59 and then fed to the outlet port.

Figure 12:
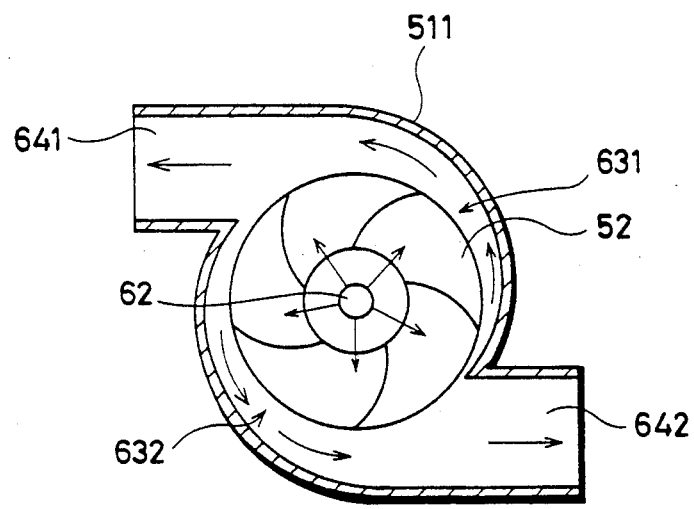
FIG. 12 is a sectional view showing the structure of the scroll chamber in accordance with the modified example of the second embodiment.

In the second embodiment, as well as the first embodiment, a plurality of scroll chambers may be arranged symmetrically with respect to the center of the impeller. FIG. 12 shows the cross section of the pump provided with a plurality of scroll chambers. In FIG. 12, when the impeller 52 rotates in a casing 511, the fluid is sucked from a suction port 62, and then fed via scroll chambers 631, 632 into outlet ports 641, 642. In this example, the impeller may be rotated in an extremely stable manner.

The scroll chamber having the configuration shown in FIG. 9 may be applied to the pump shown in FIG. 10.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A pump, comprising:
   a rotating member having blades providing energy to a fluid, and adapted to be capable of receiving a magnetic action from the outside;
   a casing for housing said rotating member;
   means for supporting said rotating member from outside of said casing in a non-contacting manner with said casing; and
   rotatable means for magnetically rotating said rotating member from outside of said casing.

2. A pump according to claim 1, wherein:
   said casing includes a plurality of scroll chambers arranged symmetrically with respect to an axis of rotation of said rotation member for guiding a fluid provided with energy by said rotating member.

3. A pump, comprising:
   a rotating member having blades providing energy to a fluid, having one plane including a plurality of permanent magnets and the other plane including a magnetic member;
   a casing made of a non-magnetic material for housing said rotating member;
   rotation driving means for rotating said rotating member, said rotation driving means being rotatable and including a plurality of magnets opposed to said permanent magnets of said rotating member over said casing, said magnet of said rotation driving means magnetically coupling with said permanent magnet of said rotating member; and
   supporting means for magnetically supporting said rotating member in said casing in an non-contacting manner, said supporting means including a plurality of electromagnets opposed to said magnetic member of said rotating member over said casing, said plurality of electromagnets acting in such a way that said rotating member is supported, spaced from said casing.

4. A pump according to claim 3, wherein:
   each of said plurality of permanent magnets of said rotating member is arranged on a predetermined circumference with respect to the axis of rotation of said rotating member.

5. A pump according to claim 4, wherein:
   said plurality of permanent magnets of said rotating member are magnetized in such a way that the directions of the magnetic fields of adjoining ones are opposite to each other.

6. A pump according to claim 3, wherein:
at least three of said electromagnets are provided thereby forming a 3-axis controlled magnetic bearing.

7. A pump according to claim 6, further comprising:
detection means for detecting the space between said rotating member and said casing, and supplying a detection signal corresponding to the space detected; and
control means responsive to the detection signal from said detection means for controlling the value of the current applied to said electromagnet.

8. A pump according to claim 3, wherein:
said casing includes a plurality of scroll chambers arranged symmetrically with respect to the axis of rotation of said rotating member for feeding a fluid provided with energy by said rotating member.

9. A pump, comprising:
a rotating member with blades providing energy to a fluid, having one plane including a plurality of permanent magnets and the other plane including a magnetic member;
a casing made of a non-magnetic material for housing said rotating member;
rotation driving means for rotating said rotating member, said rotation driving means including a plurality of stator windings opposed to said one plane of said rotating member over said casing for generating a rotating magnetic field; and
supporting means for magnetically supporting said rotating member in said casing in a non-contacting manner, said supporting means including a plurality of electromagnets opposed to said magnetic member of said rotating member over said casing, and said plurality of electromagnets acting in such a way that said rotating member is supported, spaced from said casing.

10. A pump according to claim 9, wherein:
each of said plurality of permanent magnets of said rotating member is arranged on a predetermined circumference with respect to the axis of rotation of said rotating member.

11. A pump according to claim 9, wherein:
said plurality of permanent magnets of said rotating member are magnetized in such a way that the directions of the magnetic fields of adjoining ones are opposite to each other.

12. A pump according to claim 9, wherein:
the number of said plurality of permanent magnets is 1.5 times of the number of said plurality of stator winding.

13. A pump according to claim 9, wherein:
at least three of said electromagnets are providing, thereby forming a 3-axis controlled magnetic bearing.

14. A pump according to claim 13 further comprising:
detection means for detecting the space between said rotating member and said casing, and supplying a detection signal corresponding to the detected space; and
control means responsive to the detection signal from said detection means for controlling the value of the current applied to said electromagnet.

15. A pump according to claim 9, wherein:
said casing includes a plurality of scroll chambers arranged symmetrically with respect to the axis of rotation of said rotating member for feeding a fluid provided with energy by said rotating member.

* * * * *